US008657853B2

(12) United States Patent
Straehnz

(10) Patent No.: US 8,657,853 B2
(45) Date of Patent: Feb. 25, 2014

(54) INCISION CLOSURE DEVICE AND METHOD

(75) Inventor: Jens-Peter Straehnz, Bremen (DE)

(73) Assignee: Ethicon, Inc., Somerville, NJ (US)

( * ) Notice: Subject to any disclaimer, the term of this patent is extended or adjusted under 35 U.S.C. 154(b) by 324 days.

(21) Appl. No.: 12/476,826

(22) Filed: Jun. 2, 2009

(65) Prior Publication Data

US 2010/0305587 A1   Dec. 2, 2010

(51) Int. Cl.
*A61B 17/08* (2006.01)
(52) U.S. Cl.
USPC .......................................................... 606/216
(58) Field of Classification Search
USPC ............ 606/151, 213–221; 623/23.72, 23.75; 602/41–44, 47, 48, 56, 58, 59, 76
See application file for complete search history.

(56) References Cited

U.S. PATENT DOCUMENTS

| | | | | |
|---|---|---|---|---|
| 4,467,805 A * | 8/1984 | Fukuda | | 606/217 |
| 4,676,245 A * | 6/1987 | Fukuda | | 606/216 |
| 5,263,969 A * | 11/1993 | Phillips | | 606/213 |
| 5,441,508 A | 8/1995 | Gazielly et al. | | |
| 5,840,011 A * | 11/1998 | Landgrebe et al. | | 600/30 |
| 6,808,487 B2 | 10/2004 | Migliari | | |
| 7,105,001 B2 | 9/2006 | Mandelbaum | | |
| 7,131,943 B2 | 11/2006 | Kammerer | | |
| 7,500,993 B2 | 3/2009 | De la Torre et al. | | |
| 2002/0049503 A1 * | 4/2002 | Milbocker | | 623/23.72 |
| 2003/0065360 A1 * | 4/2003 | Jacobs et al. | | 606/216 |
| 2004/0039453 A1 | 2/2004 | Anderson et al. | | |
| 2004/0204740 A1 * | 10/2004 | Weiser | | 606/213 |
| 2005/0021083 A1 * | 1/2005 | Lebner | | 606/216 |
| 2005/0277965 A1 | 12/2005 | Brenneman et al. | | |
| 2007/0038246 A1 * | 2/2007 | Lebner et al. | | 606/215 |
| 2007/0213750 A1 | 9/2007 | Weadock | | |
| 2007/0225761 A1 * | 9/2007 | Shetty | | 606/219 |
| 2008/0021265 A1 | 1/2008 | Garbin et al. | | |
| 2008/0065153 A1 * | 3/2008 | Allard et al. | | 606/219 |
| 2008/0228219 A1 * | 9/2008 | Weiser | | 606/215 |

FOREIGN PATENT DOCUMENTS

| | | |
|---|---|---|
| DE | 2418603 A1 | 10/1975 |
| WO | WO 0106951 A1 | 2/2001 |
| WO | 2006/121855 A2 | 11/2006 |

OTHER PUBLICATIONS

Engemann, R, et al., "Incidence, Pathogenesis and Prophylaxis of Incitional Hernias", Langenbecks Arch Chir Suppl. (1993) 263-267.
Yuce, K, "Retention Mesh: An Alternative to Retention Sutures", Eur. J. Surg (1994) 160: 641-642.
Zienowicz, R. J., et al. "Hernia Prevention and Aesthetic Contouring of the Abdomen Following TRAM Flap Breast Reconstruction by the Use of Polypropylene Mesh", (1993), 1346-1350.

(Continued)

*Primary Examiner* — Thomas McEvoy
*Assistant Examiner* — Jocelin Tanner

(57) ABSTRACT

A surgical incision closure device and method for using the same, having first and second elements adapted for positioning on first and second sides of the incision respectively. The first element is substantially flat and includes a first longitudinal portion extending in a longitudinal direction, and at least first and second arm portions each extending substantially perpendicularly outward from the first portion and spaced apart from one another. The second element is substantially flat and includes a second longitudinal portion extending in the longitudinal direction, and at least third and fourth arm portions extending substantially perpendicularly outward from the second portion and spaced apart from one another.

12 Claims, 4 Drawing Sheets

(56) References Cited

OTHER PUBLICATIONS

El-Khadrawy, O. H., et al. "Prophylactic Prosthetic Reinforcement of Midline Abdominal Incisions in High-Risk Patients", Tanta Medical Sciences Journal vol. (1), No. (4), (2006) 182-192.

Gutierrez De La Pena, C. et al., "Primary closure of laparotomies with high risk of incisional hernia using prosthetic material: analysis of usefulness" Hernia (2003) 7: 134-136.

Carlson, M.A., "New developments in abdominal wall closure", Chirurg (2000) 71:743-753.

Israelsson, L.A. et al., "Closure of midline laparotomy incisions with polydioxanone and nylon: the importance of suture technique", British Journal of Surgery (1994), 81, 1606-1608.

Hodgson, N.C.F., et al."The Search for an Ideal Method of Abdominal Fascial Closure", Analysis of Surgery,(2000) vol. 231, No. 3, 436-442.

Bucknall, T.E. "Abdominal wound closure: choice of suture" Journal of the Royal Society of Medicine, (1981) vol. 74, 580-585.

Wadstrom, J. et al. "Closure of the Abdominal Wall; How and Why?" Acta Chir Scand 156: 75-82 (1990).

Dubay, D. A. et al., "The Prevention of Incisional Hernia Formation Using a Delayed-Release Polymer of Basic Fibroblast Growth Factor" Annals of Surgery, vol. 240, No. 1 (2004) 179-186.

Hodgson, N.C.F. et al., "Current practice of abdominal fascial closure: a survey of Ontario general surgeons", Journal Canadien de Chirurgie, vol. 44, No. 5 (2001) 366-370.

Hoer, J. et al., "Prophylaxe der Narbenhernie" Chirurg (2002) 73:: 881-887.

Hsiao, W-C. et al., "Incisional Hernia after Laparotomy: Prospective Randomized Comparision between Early-absorbable and Late-absorbable Suture Materials", World Journal of Surgery 24, 747-752 (2000).

Israelsson, L.A. "Abdominal Closure and Incisional Hernia" Eur. Surg. vol. 35, No. 1 (2003) 5-10.

Jenkins, T.P.N. "The burst abdominal wound: a mechanical approach" Br. J. Surg. vol. 63 (1976) 873-876.

Kingsnorth, A. "The management of incisional hernia" Ann R. Coll. Surg. Engl. (2006) 88: 252-260.

Rogers, M. et al. "Prevention of Incisional Hernia after Aortic Aneurysm Repair" Eur. J. Vasc. Endovasc Surg. 26, 519-522 (2003).

Strzelczyk, J.M. et al., "Randomized clinical trial of postoperative hernia prophylaxis in open bariatric surgery" British Journal of Surgery (2006) 93: 1347-1350.

Strzelczyk, J. et al., "The use of polypropylene mesh in midline incision closure following gastric by-pass surgery reduces the risk of postoperative hernia" Langenbecks Arch Surg (2002) 387: 294-297.

Kyzer S. et al. "The influence of peritoneal closure on formation of intraperitoneal adhesions: an experimental study" PubMed (abstract only).

Bellon, J.M. et al. "Midline abdominal wall closure: a new prophylactic mesh concept" PubMed (abstract only).

Chowdhury S.K. et al., "Mass closure versus layer closure of abdominal wound: a prospective clinical study" PubMed (abstract only).

Wadstrom J. et al. Closure of the abdominal wall; how and why? Clinical review—PubMed (abstract only).

Hugh, T. B. et al., "Is Closure of the Peritoneal Layer Necessary in the Repair of Midline Surgical Abdominal Wounds?" World J. Surg. 14, 231-234 (1990).

Written Opinion of the International Searching Authority for International Application No. PCT/US2010/035934 mailed Aug. 17, 2010.

* cited by examiner

INCISION CLOSURE DEVICE AND METHOD

BACKGROUND OF THE INVENTION

1. Field of the Invention

The present invention relates generally to surgical devices and methods for closing relatively large incisions, such as abdominal laparotomies.

2. Background Discussion

A laparotomy is a surgical incision in the abdominal cavity typically performed for the purpose of surgical treatment of abdominal organs, examination of abdominal organs, and/or to aid in diagnosis of any problems such as abdominal pain. The most typical type of incision is a midline, or vertical incision, that may be four to ten inches in length. Following the procedure, the incision must be closed, with the most common form of closure being with surgical sutures. Because of the length and depth of the incision, however, and the muscular nature of the abdominal area, the surgical sutures can experience significant tension during the recovery period of wound healing. This is particularly true when there is excessive swelling, or edema, or inflammation; in obese patients; or during normal expansion of the abdominal wall as can occur during breathing, coughing, bowel movements, heavy lifting etc. When under tension, the incisional repair can be compromised or even fail, due to the "sawing" effect of the sutures on the tissue. The situation is exacerbated in patients with multiple co-morbidities and compromised tissue integrity, such as in patient's having diabetes, cancer, immunodeficiency, older patients etc. The result of failure or partial failure often is an incisional hernia, where tissues or organs of the abdomen, mostly fatty tissue from the omentum or bowel, protrude through the hernia defect. The hernia appears as a bulge under the skin, and can be painful or tender to the touch. In case of strangulation or incarceration of hernia contents, this might even lead to life threatening situations that require emergency surgery.

In some instances, surgical meshes have been used in the conventional manner to lower the rate of incisional hernias. Meshes used in the conventional manner, however, leave behind a substantial amount of foreign body material in the patient, which has its own drawbacks such as increased risk of infection, chronic pain or discomfort. Further, a large amount of tissue dissection is required to place such meshes, the trauma of which leads to increased tissue inflammation. Finally, the extensive tissue dissection also requires a significant amount of time to properly place the mesh.

Accordingly, what is needed is an improved device and method for closure of large incisions such as abdominal laparotomies.

SUMMARY OF THE INVENTION

The present invention provides a surgical incision closure device for approximating an incision, including a first element adapted for positioning on a first side of said incision, and a second element adapted for positioning on a second side of said incision. The first element is substantially flat and made of a biocompatible material, and further includes a first longitudinal portion having a length and a width and extending in a longitudinal direction, and at least first and second arm portions each having a length and a width and extending substantially perpendicularly outward from the first portion and spaced apart from one another. The second element is substantially flat and made of a biocompatible material and further includes a second longitudinal portion having a length and a width and extending in the longitudinal direction, and at least third and fourth arm portions each having a length and a width extending substantially perpendicularly outward from the second portion and spaced apart from one another.

The device may be made of a biocompatible mesh that may further be made of a non-absorbable material selected from the group consisting of polypropylene, polyalkenes, polyethylene, fluorinated polyolefins, polytetrafluoroethylene, polyvinylidenefluoride, polyamides, polyurethanes, polyisoprenes, polystryrenes, polysilicones, polycarbonates, polyaryletherketones, polymetacrylates, polyacrylates, aromatic polyesters, polyimides, and copolymers or polymerisable substances thereof. Alternatively, the biocompatible mesh may be made of a combination of absorbable and non-absorbable materials.

In one embodiment, the first and second longitudinal portions further include a different, absorbable material on one or both sides of the mesh, and in yet another embodiment, a distal portion of the at least first, second, third and fourth arms further include the different, absorbable material positioned on one or both sides of the mesh. The different, absorbable material may be a fleece-like material made of a combination of polygalactin and poly p-dioxanone.

In yet another embodiment, the first and second longitudinal portions have a plurality of apertures therethrough along the length thereof, and/or the distal portions of the at least first, second, third and fourth arms have an aperture therethrough.

According to yet another embodiment, the first and second elements are substantially identical in size and shape.

The plurality of arms of the first and second elements may be spaced apart by at least 1.2 to 2 inches, and the plurality of arms may have a length of at least 2 inches.

Further, the first and second longitudinal portions may have a length and width of between about 3-10 and 0.2-0.6 inches, respectively.

Also provided is a method for repairing a surgical incision, including acquiring a device having a substantially flat first element adapted for positioning on the first side of the incision, and a substantially flat second element adapted for positioning on the second side of the incisions, wherein the first element has a first longitudinal portion having a length and a width and extends in a longitudinal direction, and at least first and second arm portions each having a length and a width and extending substantially perpendicularly outward from the first portion and spaced apart from one another, and wherein the second element has a second longitudinal portion having a length and a width and extends in the longitudinal direction, and at least third and fourth arm portions each having a length and a width extending substantially perpendicularly outward from the second portion and spaced apart from one another. The method further includes placing the first element on a first side of the incision so that the first longitudinal portion extends substantially along the incision and the at least first and second arm portions extend outwardly away from the incision, placing the second element on a second side of the incision so that the second longitudinal portion extends substantially along the incision and the at least third and fourth arm portions extend outwardly away from the incision, inserting the at least first and second arms substantially into a retromuscular layer on the first side of the incision, inserting the at least third and fourth arms substantially into the retromuscular layer on the second side of the incision, and attaching the first and second longitudinal portions to one another at the surface of the incisions to thereby approximate the incision.

Also provided is a kit for surgical incision closure including a closure device including a substantially flat first element adapted for positioning on a first side of the incision, and a substantially flat second element adapted for positioning on a second side of the incision. The first element further includes a first longitudinal portion having a length and a width and extending in a longitudinal direction, and at least first and second arm portions each having a length and a width and extending substantially perpendicularly outward from the first portion and spaced apart from one another, and the second element further includes a second longitudinal portion having a length and a width and extending in the longitudinal direction, and at least third and fourth arm portions each having a length and a width extending substantially perpendicularly outward from the second portion and spaced apart from one another. The first and second elements are made of a bio-compatible material. The kit further includes an inserter device having a handle and a distal end portion, wherein the distal end portion is adapted to be removably coupled with each of the at least first, second third and fourth arm portions of the closure device.

These and other features and advantages of the present invention will become apparent from the following more detailed description, when taken in conjunction with the accompanying drawings which illustrate, by way of example, the principles of the invention.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, although the present invention is described in detail in relation to laparotomy incisions in particular, it is to be understood that it can be readily adapted for use in any types of abdominal incisions (i.e., c-section incisions), and any other relatively long incision.

Figure 1:
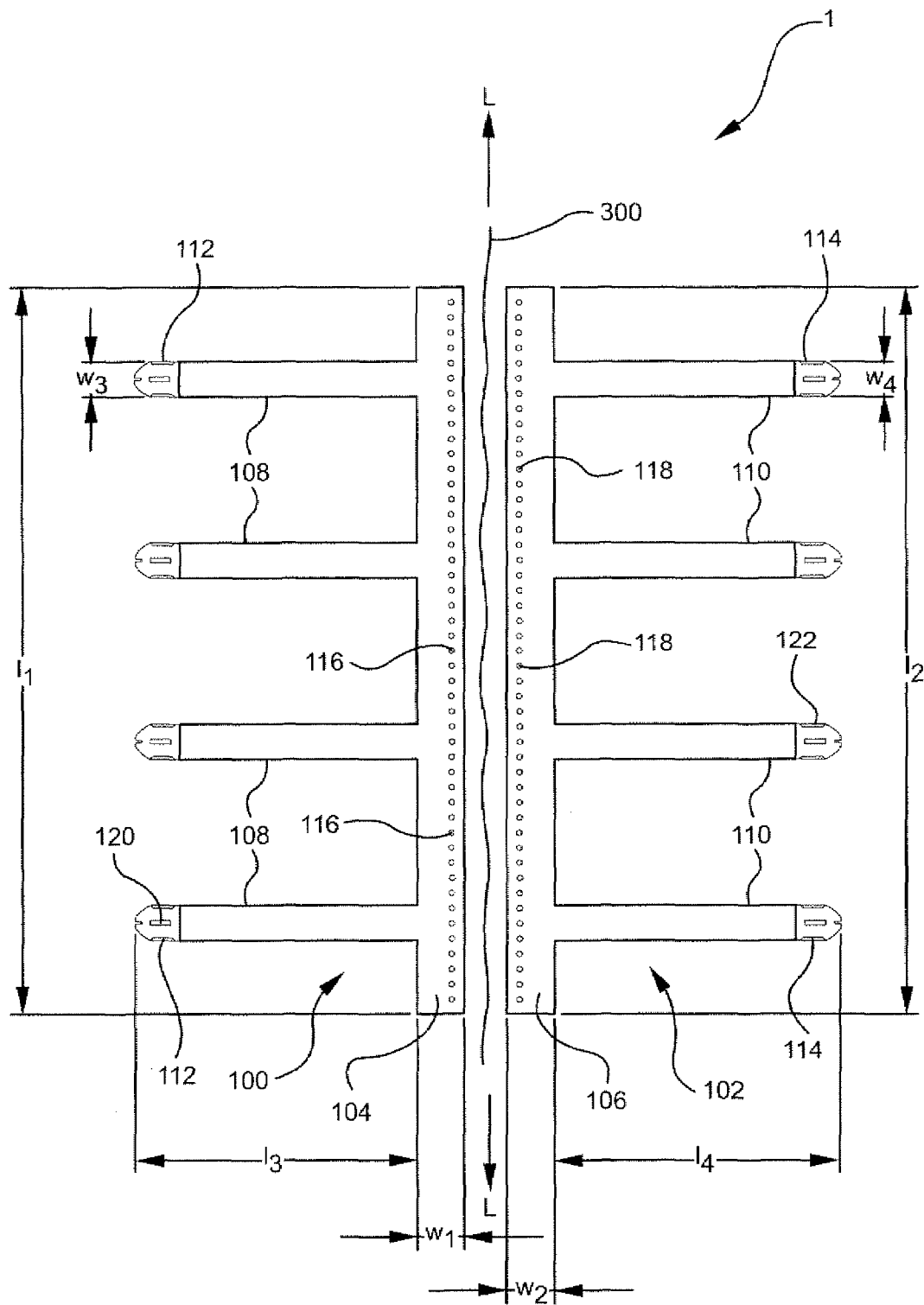
FIG. 1 illustrates an exemplary embodiment of a device for laparotomy closure according to the present invention.

FIG. 1 illustrates an exemplary device for incision closure according to the present invention. The device 1 includes a first element 100 and a second element 102 adapted for placement on first and second sides of an incision respectively. The first element has a first longitudinal portion 104 having a width $w_1$ and a length $l_1$ and extending in longitudinal direction L, and at least first and second arms 108 extending outwardly therefrom. The at least first and second arms preferably extend outwardly in a substantially perpendicular direction from the longitudinal direction L, and are preferably spaced apart from one another as shown. The second element 102 similarly includes a second longitudinal portion 106 having a width $w_2$ and a length $l_2$ and extending in longitudinal direction L. At least third and fourth arms 110 extend outwardly in a substantially perpendicular direction from the longitudinal direction L, and in the opposite direction from the first and second arms 108. Although FIG. 1 illustrates a device with four arms on each side, it is to be understood that the device could include only two arms on each side, or any number greater than that, the number of which can be tailored to the size and type of incision requiring closure. Further, a device with many arms can be cut by the user or surgeon at the surgical site in order to best customize the size of the device.

The device may be made of any suitable biocompatible material having sufficient mechanical properties. Preferably, the device is comprised of an absorbable or non-absorbable mesh material, or some combination thereof. Exemplary mesh materials include PROLENE®, which is a knitted or woven polypropylene mesh having a thickness of approximately 0.7 mm, and which is manufactured by Ethicon, Inc. of Somerville, N.J. Other suitable materials include non absorbable substances such as polyalkenes, polyethylene, fluorinated polyolefins, polytetrafluoroethylene, polyvinylidenefluoride, polyamides, polyurethanes, polyisoprenes, polystryrenes, polysilicones, polycarbonates, polyaryletherketones, polymetacrylates, polyacrylates, aromatic polyesters, polyimides, and copolymers of polymerisable substances thereof. Further, suitable absorbable materials include polyhydroxy acids, polylactides, polyglycolides, polyhydroybutyrates, polyhydroxyvaleriates, polycaprolactones, polydioxanones, synthetic and natural oligo- and polyaminoacids, polyphosphazenes, polyanhydrides, polyorthoesters, polyphosphates, polyphosphonates, polyalcohols, polysaccharides, polyethers, resorbable glasses, and copolymers of polymerisable substances thereof. Other textile technologies incorporating non-woven techniques may also be suitable.

In a preferred embodiment, one or both sides of the first and second longitudinal portions are reinforced with an absorbable material designed to promote tissue ingrowth. One suitable material for such reinforcement is created by assembling material or components of a product sold under the name ETHISORB® Dura Patch (sold by Codman & Shurtleff, Inc. of Raynham, Ma.), which is mainly a VICRYL® polyglactin synthetic surgical composite material that is used for tissue reinforcement surgery. VICRYL® is a material that is also manufactured by Ethicon, Inc. ETHISORB® Dura Patch includes a fleece made from VICRYL® (polyglactin 910) and PDS (poly p-dioxanone) undyed yarn which is sandwiched on one side with a piece of dyed poly-p-dioxanone film. The fleece and film are bonded together in a process that leaves the film intact as a sheet. In one embodiment, first and second longitudinal portions of the device 1 are sandwiched between two pieces of ETHISORB® Dura Patch with the components being thermally bonded together. In an alternate embodiment, the device is made of PROLENE® mesh, and the separate components (fleece pad and the dyed poly-p-dioxanone film sheet) are placed on one side of the longitudinal portions of the device, and a second fleece pad and dyed poly-p-dioxanone film sheet are placed on other side. The 5-piece assembly is then placed into a thermal process to bond the components together. The thermal process is controlled to maintain the temperature such that it only will melt the PDS yarn and dyed poly-p-dioxanone film. Use of the separate components provides a non-pressed fleece that facilitates subsequent bonding of the two film sheets through the mesh, since the two fluffy fleece layers integrate into the weave of the PROLENE® mesh during pressing. After the thermal pressing process, the dyed poly-p-dioxanone film sheets no longer exist, as they are melted forming a plethora of bond points between the mesh and fleece layers.

Each of the first and second longitudinal portions may further include a plurality of apertures 116, 118 therethrough and along the length thereof that help the surgeon with suture placement as will be described further below. Finally, distal portions 112, 114 of the plurality of arms may similarly be reinforced with an absorbable material designed to facilitate tissue ingrowth, such as that described above.

In a preferred embodiment, the length of the first and second longitudinal portions 104,106 is at least three inches, and preferably 3.0 to 10 inches, although as described above it may be made longer, allowing the surgeon to trim it down as deemed necessary. The width $w_1$, $w_2$ of the longitudinal portions is preferably about 0.6 inches, and the lengths $l_3$, $l_4$ are approximately 2-4 inches] and width $w_3$, $w_4$ of the arm portions is preferably about 0.2 inches each. As is apparent from FIG. 1, the collective widths of the arm portions is intended to be significantly less than the length of the longitudinal portions in order to minimize the foreign material that is implanted within the body. Further, the arms are spaced apart along the length of the longitudinal portions in order to better distribute the forces along the length thereof as will be described further below.

Figure 2:
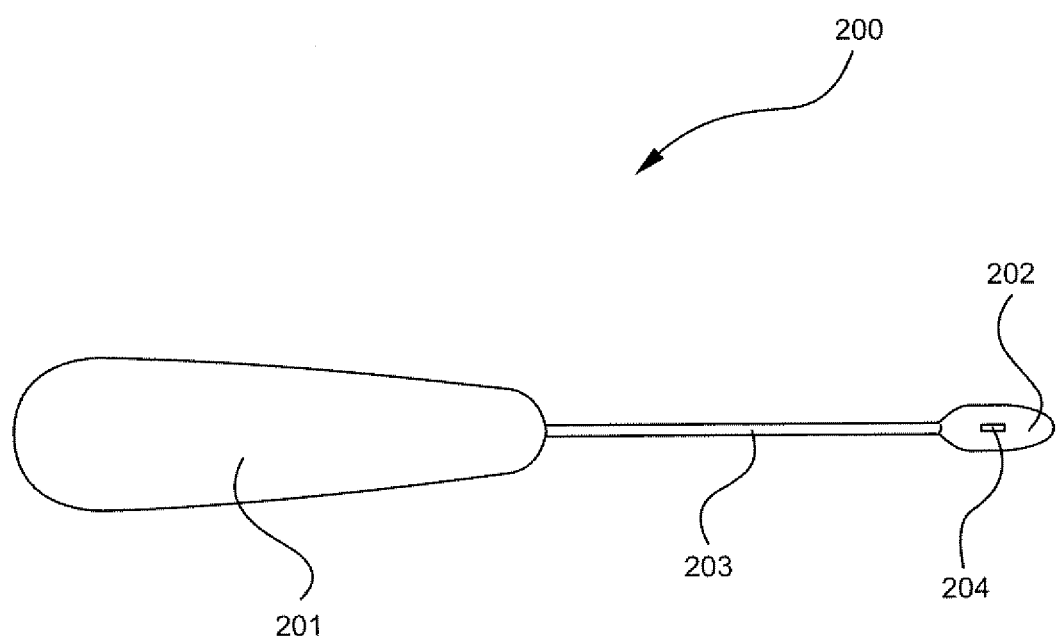
FIG. 2 illustrates an exemplary instrument that can be used to assist in placing the device of FIG. 1.

Referring now to FIG. 2, an exemplary instrument 200 is shown that can be used to aid in placement of the device described above. The instrument includes a handle portion 201 and a distal portion 202 that is designed to engage the distal portions 112, 114 of the arms of the device, and a central portion 203 extending therebetween. The distal portion 202 is preferably of a size and shape that substantially matches that of the distal portions 112, 114 of the arms. It may be slightly smaller, but should be sufficiently sized to maintain a substantially flat orientation of the distal portion of the arms as they are implanted. In a preferred embodiment, the distal portion includes a projection 204 or the like that is designed to extend through a apertures 120, 122 in the distal portions of the arms. This enables the inserter to removably engage the distal portion of the arms and push it through the tissue during implantation. Although a projection is illustrated and described herein, those skilled in the art will readily understand various other means by which to removably secure the instrument to the arms of the device during implantation, and the present invention is not intended to be so limited.

Figure 3A:
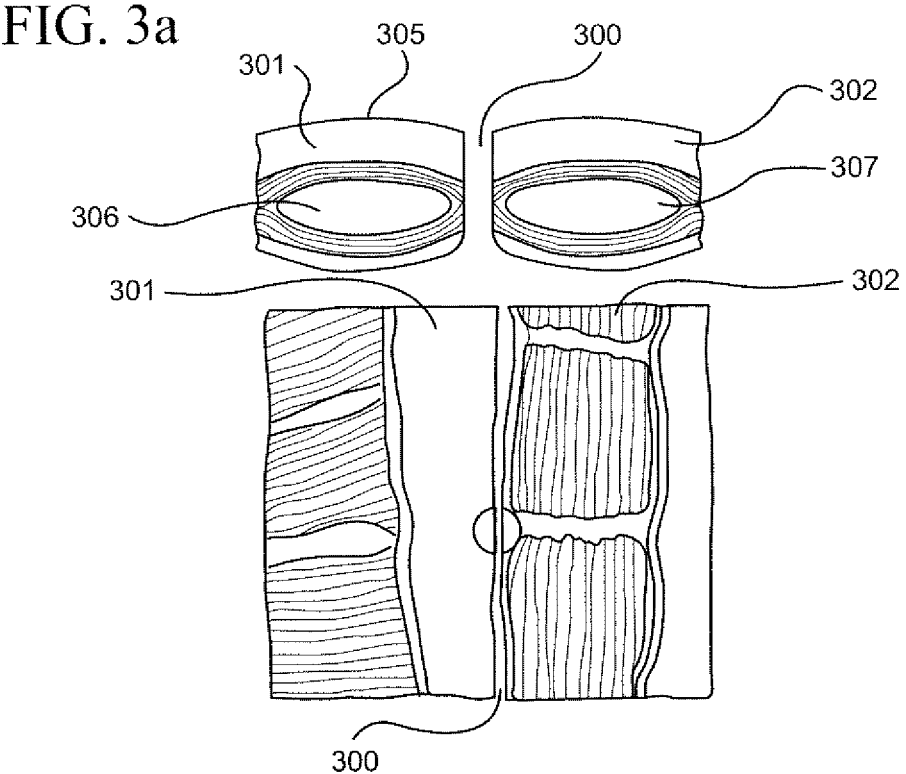
FIGS. 3a-3c are top and cross-sectional views of an abdominal incision, and illustrate various steps for placing the device of FIG. 1 to close the incision.
Figure 3B:
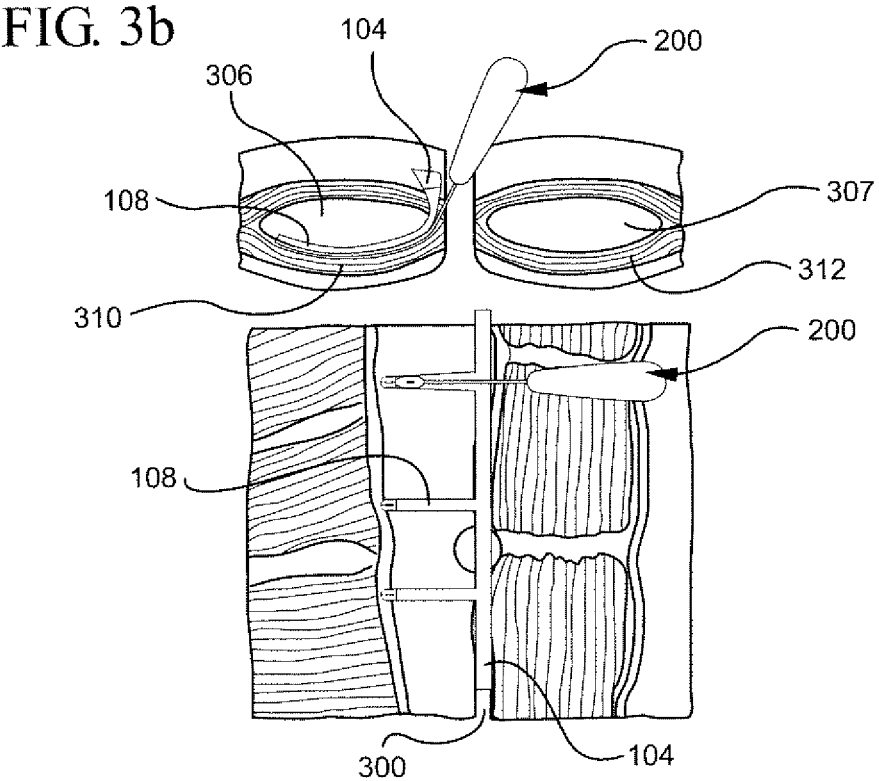
Figure 3C:
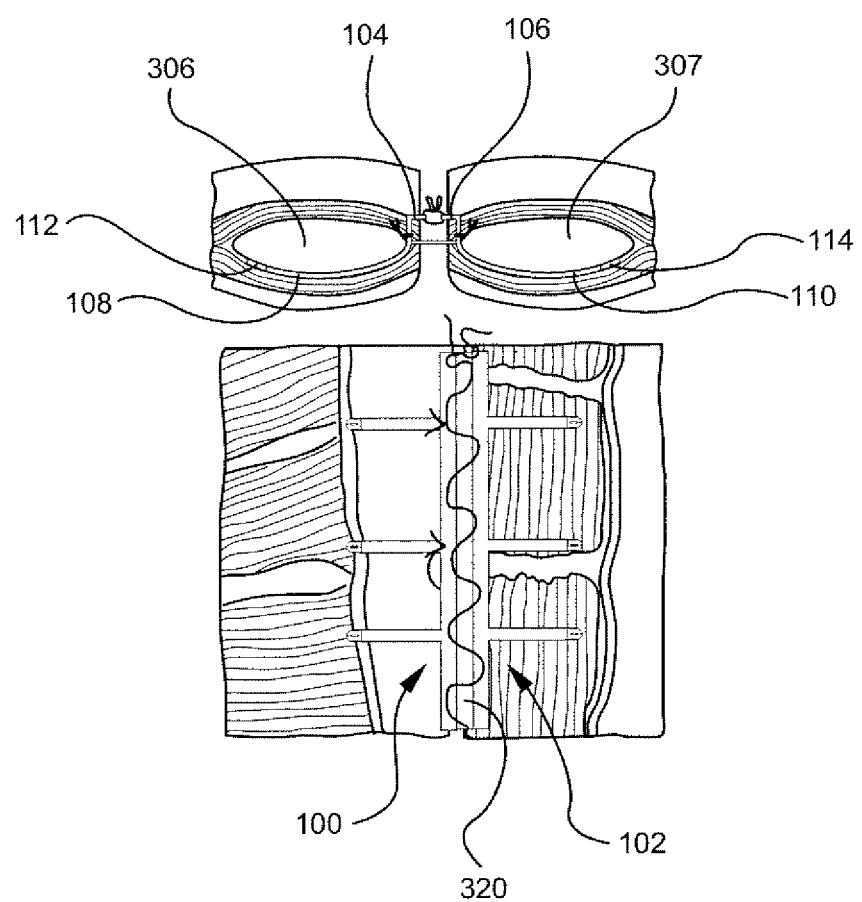

FIGS. 3a-3c are top and cross-sectional views of an incision showing various steps in a method for implanting incision closure devices of the present invention. Referring first to FIG. 3a, incision 300 and first and second sides 301, 302 thereof are shown with the surface of the skin being shown by reference numeral 305. Beneath the skin (epidermis) on each side of the incision, is subcutaneous tissue, and beneath that is the anterior fascia 320 of the abdominal wall muscles, which, on both sides of the midline, is called the linea alba 321. The abdominal rectal muscle is shown by reference numeral 306.

The first and second elements 100, 102 of the device 1 are longitudinally aligned with the incision the first and second sides 301, 302 respectively, and more particularly, are preferably aligned with the linea alba. This can also be seen in FIG. 1, wherein line 300 represents the incision line. Once properly aligned, small incisions are made in the ventral fascia of the abdominal rectal muscle and the at least first and second arms 108 of the first element 100 are then placed into the retromuscular space below the abdominal rectal muscle as illustrated in FIG. 3b. Preferably, the arms are place just into the retromuscular layer in the plane defined by the retromuscular layer and fascia 310, 312 as shown, and are preferably placed using an inserter 200 such as the one shown in FIG. 2. This placement minimizes tissue damage, and benefits from intra-abdominal pressure to help hold the ends in place as the inserter device is removed. The first longitudinal portion remains on the ventral fascia of the abdominal rectal muscle/ linea alba as shown in FIG. 3c. The same procedure is repeated on the second side 302 of the incision using the second element 102 until placement is complete as shown in FIG. 3c. Following final placement, preferably one running suture 320 is used to suture the first and second longitudinal portions to the underlying tissue, and also to each other to approximate the tissue of the linea alba just as it is used in a standard closure technique for the closing of the laparotomy. As mentioned previously, the device may include a plurality of apertures along the length of the first and second longitudinal portions to assist in placement of the sutures. The device could also be placed in the preperitoneal space with a slightly different application technique.

What is claimed is:

1. A surgical incision closure device for approximating an incision in a patient, comprising:
   a first element adapted for positioning on a first side of said incision, and a second element adapted for positioning on a second side of said incision, wherein said first and second elements are not physically coupled to one another;
   wherein the first element is substantially flat and includes a first longitudinal portion having first and second opposing edges extending along a length thereof and third and fourth opposing edges extending along a width thereof, said first element extending in a longitudinal direction, and adapted to be substantially aligned with a length of said incision and positioned on a surface of a skin of said patient on a first side of the incision, and at least first and second arm portions each having a length and a width and extending substantially perpendicularly outward from the first edge of the first portion and spaced apart from one another, and at least distal ends thereof adapted to be implanted beneath the skin of the patient on an opposite side of the incision from the first longitudinal portion;
   wherein the second element is substantially flat and includes a second longitudinal portion having first and second opposing edges extending along a length thereof and third and fourth opposing edges extending along a width thereof, said second element extending in said longitudinal direction, and adapted to be substantially aligned with the length of the incision and positioned on the surface of the skin of the patient on said opposite side of the incision, and at least third and fourth arm portions each having a length and a width extending substantially perpendicularly outward from said first edge of the second portion and spaced apart from one another, and at least distal ends thereof adapted to be implanted beneath the skin of the patient on the first side of the incision; and
   wherein at least a portion of the first, second, third and fourth arms of the first and second elements further comprises a layer of an absorbable material adapted to promote subcuticular tissue ingrowth therein adjacent at least one side thereof; and
   wherein the first and second elements are comprised of a biocompatible mesh.

2. The device according to claim 1, wherein the biocompatible mesh is comprised of a non-absorbable material selected from the group consisting of polypropylene, polyalkenes, polyethylene, fluorinated polyolefins, polytetrafluoroethylene, polyvinylidenefluoride, polyamides, polyurethanes, polyisoprenes, polystryrenes, polysilicones, polycarbonates, polyaryletherketones, polymetacrylates, polyacrylates, aromatic polyesters, polyimides, and copolymers or polymerisable substances thereof.

3. The device according to claim 1, wherein the biocompatible mesh is comprised of a combination of absorbable and non-absorbable materials.

4. The device according to claim 1, wherein the first and second longitudinal portions further comprises a different, absorbable material on one or both sides of the mesh.

5. The device according to claim 4, wherein the first and second longitudinal portions have a plurality of apertures therethrough along the length thereof.

6. The device according to claim 1, wherein the distal portions of the at least first, second, third and fourth arms have an aperture therethrough.

7. The device according to claim 1, wherein the first and second elements are substantially identical in size and shape.

8. The device according to claim 7, wherein the plurality of arms of the first and second elements are spaced apart by at least 1.2 to 2 inches.

9. The device according to claim 8, wherein the plurality of arms have a length of at least 2.0 inches.

10. The device according to claim 9, wherein the first and second longitudinal portions have a length and width of between about 3.0 to 10, and 0.2-0.6 inches, respectively.

11. A kit for surgical incision closure in a patient comprising:
   a closure device including a substantially flat first element adapted for positioning on a first side of said incision, and a substantially flat second element adapted for positioning on a second side of said incision, wherein the first element further comprises a first longitudinal portion having first and second opposing edges extending along a length thereof, and third and fourth opposing edges extending along a width thereof, said first element extending in a longitudinal direction, and adapted to be substantially aligned with a length of the incision and positioned on a surface of a skin of the patient on a first side of the incision, and at least first and second arm portions each having a length and a width and extending substantially perpendicularly outward from the first edge of the first portion and spaced apart from one another, and at least distal ends thereof adapted to be implanted beneath the skin of the patient on an opposite side of the incision from the first longitudinal portion, and wherein the second element further comprises a second longitudinal portion having first and second opposing edges extending along a length thereof, and third and fourth opposing edges extending along a width thereof, said second element extending in said longitudinal direction, and adapted to be substantially aligned with the length of the incision and positioned on the surface of the skin of the patient on said opposite side of the incision, and at least third and fourth arm portions each having a length and a width extending substantially perpendicularly outward from the first edge of the second portion and spaced apart from one another, and at least distal ends thereof adapted to be implanted beneath the skin of the patient the first side of the incision, wherein the first and second elements are not physically coupled to one another; and wherein the first and second elements are comprised of a polypropylene mesh; and
   an inserter device having a handle and a distal end portion, wherein the distal end portion is adapted to be removably coupled, one at a time, with each of the at least first, second third and fourth arm portions of the closure device.

12. The kit according to claim 11, wherein the first and second elements are comprised of a mesh constructed from a combination of absorbable and non-absorbable materials.

* * * * *